United States Patent
Fazzolari

(10) Patent No.: US 8,631,941 B2
(45) Date of Patent: Jan. 21, 2014

(54) AMPOULE DISPENSER ASSEMBLY AND PROCESS

(75) Inventor: Francesca Fazzolari, Hackettstown, NJ (US)

(73) Assignee: James Alexander Corporation, Blairstown, NJ (US)

( * ) Notice: Subject to any disclaimer, the term of this patent is extended or adjusted under 35 U.S.C. 154(b) by 61 days.

(21) Appl. No.: 13/092,736

(22) Filed: Apr. 22, 2011

(65) Prior Publication Data

US 2011/0284583 A1    Nov. 24, 2011

Related U.S. Application Data

(60) Provisional application No. 61/327,001, filed on Apr. 22, 2010.

(51) Int. Cl.
  *B65D 83/04* (2006.01)
  *B65D 85/42* (2006.01)
  *B65D 1/09* (2006.01)

(52) U.S. Cl.
  USPC .................. 206/528; 206/532; 206/539

(58) Field of Classification Search
  USPC ............. 206/528, 484, 532, 438, 439, 530;
              401/132; 71/904; 221/302; 222/129,
              222/107, 189.06
  See application file for complete search history.

(56) References Cited

U.S. PATENT DOCUMENTS

| | | | |
|---|---|---|---|
| 2,395,109 A | 2/1946 | Fonda | |
| 2,546,848 A | 3/1951 | Bishop | |
| 2,670,074 A * | 2/1954 | Golden | 206/215 |
| 2,681,168 A | 6/1954 | McMillion | |
| 2,705,007 A | 3/1955 | Gerber | |
| 2,966,909 A | 1/1961 | Halperin | |
| 3,741,383 A * | 6/1973 | Wittwer | 206/219 |
| 3,813,534 A | 5/1974 | Gilliam | |
| 3,856,142 A | 12/1974 | Vessalo | |
| 3,881,634 A | 5/1975 | Thrun | |
| 3,964,643 A * | 6/1976 | Morane et al. | 222/129 |
| 4,058,425 A | 11/1977 | Thrun | |
| 4,089,415 A | 5/1978 | Laib | |
| 4,095,596 A | 6/1978 | Grayson | |
| 4,342,395 A | 8/1982 | Brown | |
| 4,751,119 A * | 6/1988 | Yukawa | 428/34.4 |
| 5,133,458 A | 7/1992 | Miller | |
| 5,379,898 A * | 1/1995 | Joulia | 206/528 |
| 6,478,191 B1 | 11/2002 | D'Alessio et al. | |
| 6,641,319 B2 | 11/2003 | May | |
| 7,581,899 B2 | 9/2009 | May et al. | |
| 7,637,679 B2 | 12/2009 | May et al. | |
| 7,976,234 B2 | 7/2011 | May | |
| 2002/0110483 A1 | 8/2002 | Aamodt et al. | |
| 2004/0244793 A1 | 12/2004 | Wedel | |
| 2005/0111900 A1 | 5/2005 | Fazzolari et al. | |
| 2009/0152267 A1 | 6/2009 | May et al. | |
| 2009/0196675 A1 | 8/2009 | May | |
| 2009/0305054 A1 * | 12/2009 | Huck | 428/426 |

* cited by examiner

*Primary Examiner* — Luan K Bui
*Assistant Examiner* — Rafael Ortiz
(74) *Attorney, Agent, or Firm* — Tejpal S. Hansra

(57) ABSTRACT

A dispenser assembly has a rupturable inner container and a cover member. The rupturable inner container contains a first flowable material. The cover member encapsulates the inner container. The cover member is impregnated with a second material, wherein the inner container is rupturable wherein the first flowable material contacts the cover member and interacts with the second material to form a mixture.

15 Claims, 5 Drawing Sheets

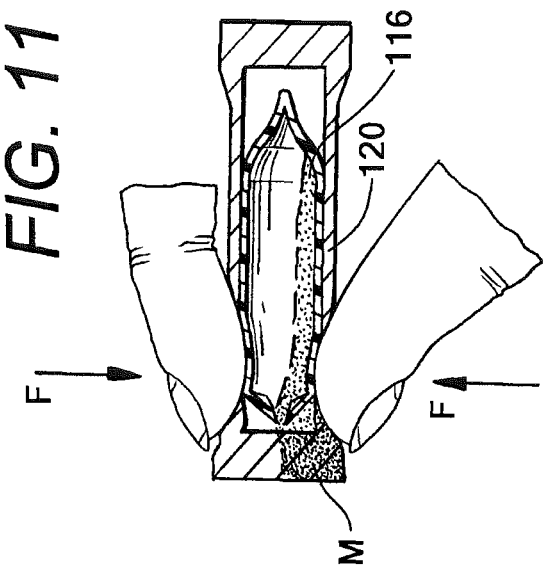
FIG. 11
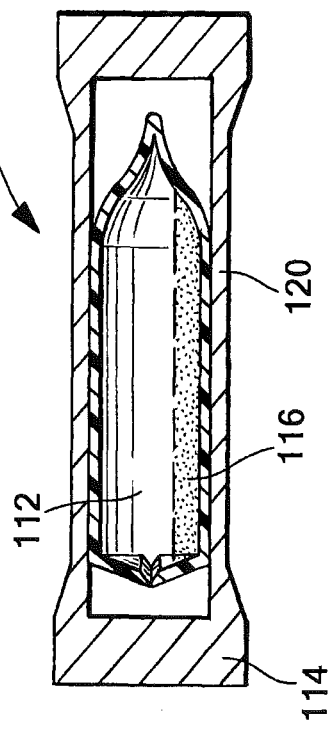
FIG. 9
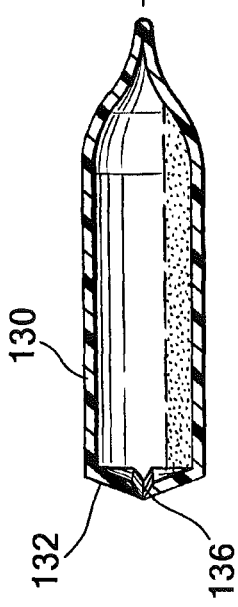
FIG. 10
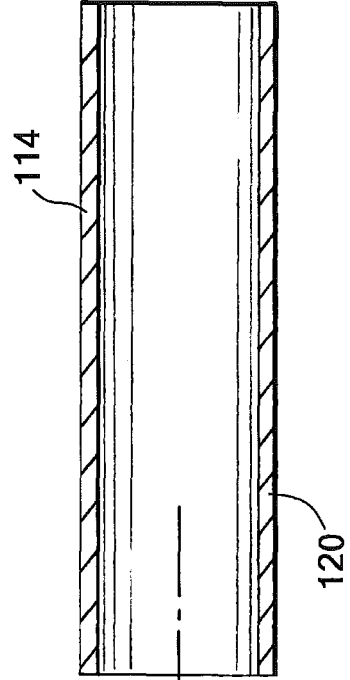

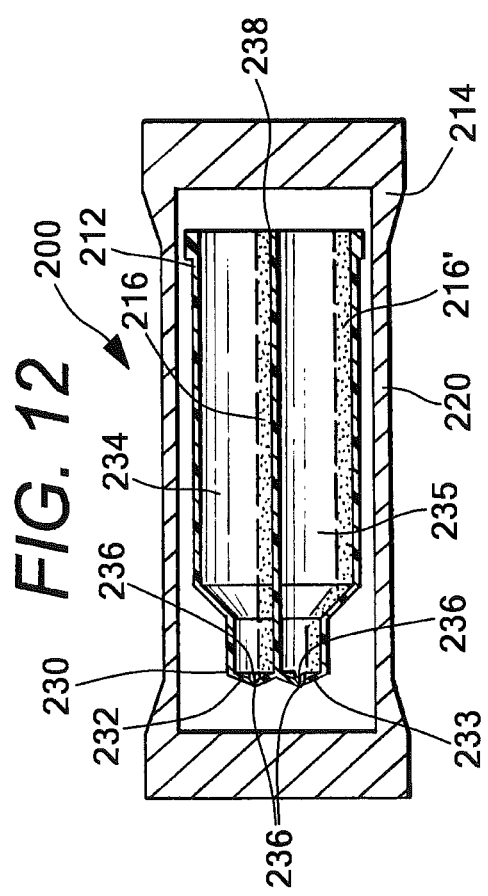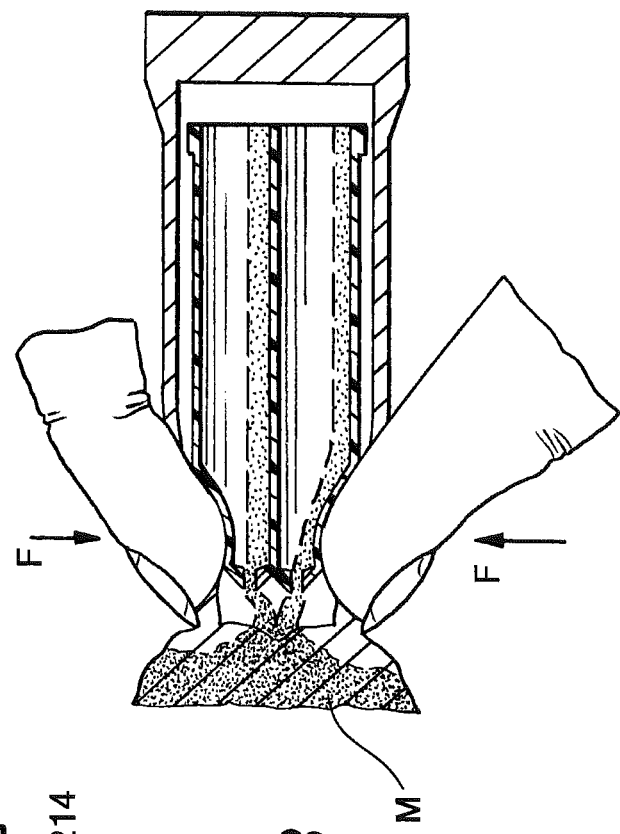

AMPOULE DISPENSER ASSEMBLY AND PROCESS

CROSS-REFERENCE TO RELATED APPLICATIONS

The present pending application claims the benefit of and claims priority to U.S. Patent Appln. No. 61/327,001, filed on Apr. 22, 2010, which application is incorporated herein by reference and made a part hereof.

FEDERALLY SPONSORED RESEARCH OR DEVELOPMENT

None.

TECHNICAL FIELD

The invention relates generally to an ampoule dispenser assembly and more particularly, to a glass ampoule containing a first flowable material and wherein the assembly has a cover impregnated with a second material, the cover encapsulating the glass ampoule.

BACKGROUND OF THE INVENTION

Ampoules are well known in the art, particularly ampoules made from glass. Ampoules are generally used to contain and dispense a flowable material once the ampoule is activated. Traditionally, however, ampoules were available in a few limited configurations and have been used only in a relatively narrow variety of uses. For example, glass ampoules have typically been used in dispensing a single flowable material. Glass ampoules have typically not been used for interacting with multiple materials.

While ampoules according to the prior art provide a number of advantageous features, they nevertheless have certain limitations. The present invention seeks to overcome certain of these limitations and other drawbacks of the prior art, and to provide new features and new uses for ampoules not heretofore available. A full discussion of the features and advantages of the present invention is deferred to the following detailed description, which proceeds with reference to the accompanying drawings.

SUMMARY OF THE INVENTION

The present invention provides an ampoule dispenser assembly having an inner container encapsulated in a cover member.

According to a first aspect of the invention, a dispenser assembly has an inner container containing a first flowable material. A cover member encapsulates the inner container wherein the cover member is impregnated with a second material. The inner container is rupturable wherein the first flowable material contacts the cover member and interacts with the second material to form a mixture.

According to a further aspect of the invention, the mixture is capable of being dispensed from the cover member. The mixture is sensory detectable from the cover member. In one exemplary embodiment, the mixture may display a particular color or change color from an initial color of the individual contents of the dispenser assembly. The mixture may emit heat or is cool. The mixture may also emit an aroma or emit sound.

According to a further aspect of the invention, the first flowable material is a liquid and the second flowable material is a powder.

According to a further aspect of the invention, the inner container is a glass ampoule and the cover member is paper-based. In an exemplary embodiment, the cover member is formed from cellulose acetate and can also be other absorbent-based materials.

According to a further aspect of the invention, the inner container may comprise a plurality of glass ampoules, each ampoule containing a flowable material.

According to another aspect of the invention, a dispenser assembly has a container having an outer wall and a membrane collectively defining a chamber configured to contain a flowable material. The membrane has thickness and a weld seam, the weld seam having a thickness less than the thickness of the membrane. The dispenser assembly also has cover member encapsulating the glass ampoule. The cover member is impregnated with a second material. The inner container is rupturable wherein the first flowable material contacts the cover member and interacts with the second material to form a mixture.

According to a further aspect of the invention, the container may have a pair of membranes cooperating with the outer wall to define a first chamber and a second chamber, each chamber containing a flowable material.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 9 is a schematic view of another embodiment of a dispenser assembly according to the present invention;

FIG. 10 is an exploded view of the dispenser assembly of FIG. 9;

FIG. 11 is a schematic view of the dispenser assembly of FIG. 9 and showing rupture of an inner container;

FIG. 12 is a schematic view of another embodiment of a dispenser assembly according to the present invention; and FIG. 13 is a schematic view of the dispenser assembly of FIG. 12 and showing rupture of a multi-chambered inner container.

DETAILED DESCRIPTION OF THE PREFERRED EMBODIMENT

Figure 1:
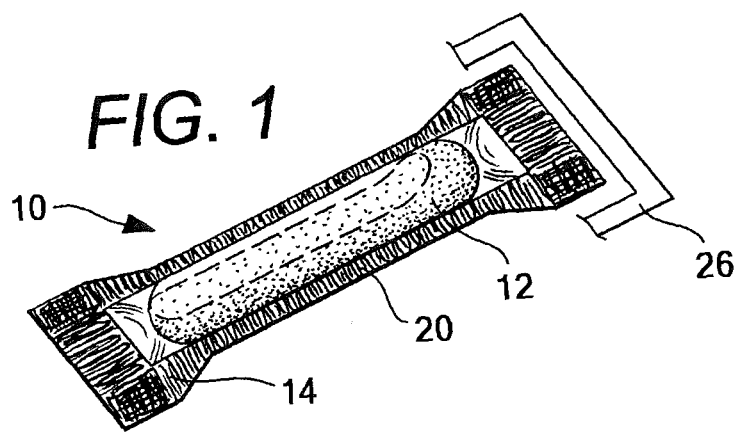
FIG. 1 is a schematic view of a dispenser assembly according to the present invention.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to the drawings, FIG. 1 discloses a dispenser assembly, generally designated with the reference numeral 10. The dispenser assembly generally includes an inner container 12 and a cover member 14. The inner container 12 and the cover member 14 are associated with materials that interact with one another as described in greater detail below.

Figure 2:
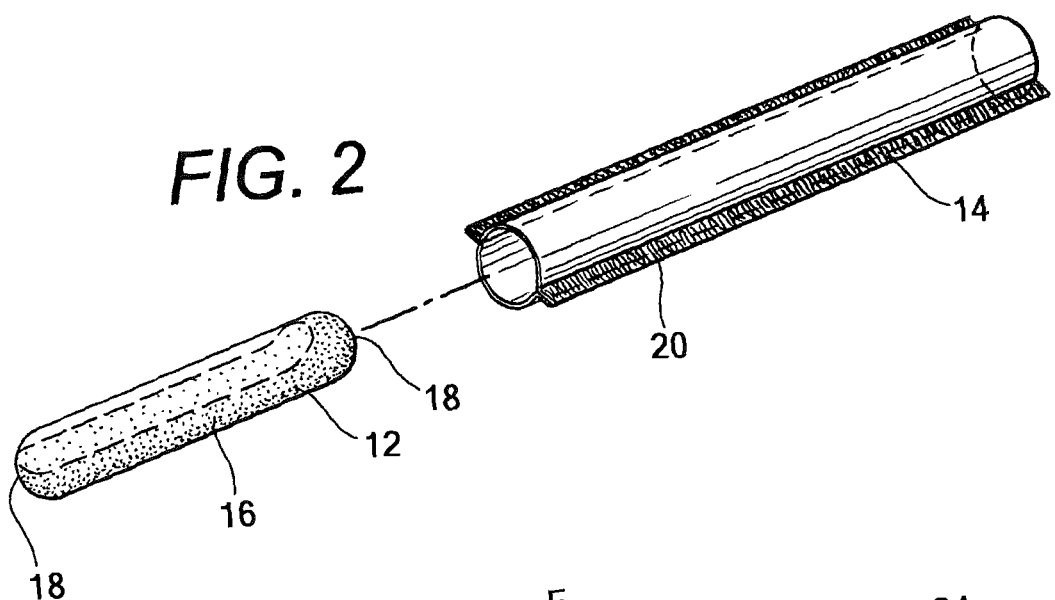
FIG. 2 is an exploded view of the dispenser assembly of FIG. 1.
Figure 3:
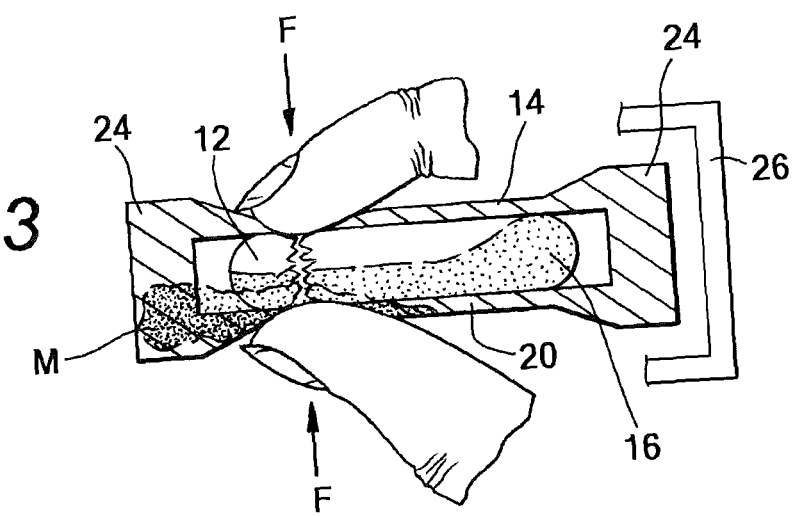
FIG. 3 is a schematic view of the dispenser assembly of FIG. 1 and showing rupture of an inner container.

As further shown in FIGS. 1-3, the inner container 12 is configured to hold a first material 16, which may be a flowable material. The inner container 12 is a rupturable container and in one exemplary embodiment, the inner container 12 is a traditional glass ampoule 12. As is known in the art, the glass ampoule 12 is generally cylindrical in form and has rounded sealed ends 18. It is understood that one end 18 is sealed wherein a first flowable material 16 is contained in the glass ampoule 12. Once the desired amount of flowable material 16 is inserted into the glass ampoule 12, the other end 18 of the glass ampoule 12 is sealed as shown in FIG. 2. It is understood that the flowable material 16 can be a liquid, powder or other type of flowable material.

The cover member 14 may be a paper-based member. In one exemplary embodiment, the cover member 14 is a cellulose acetate-based member. The member is also a porous member. If desired, the cover member 14 may have an additional paper wrap member associated therewith. Other absorbent materials could also be used as the cover member 14. Other synthetic fiber based materials could also be used. The cover member 14 may be comprised of multiple layers (FIG. 6) or a single layer. In an exemplary embodiment, the cover member 14 is impregnated with another material, or second material 20. The second material may be a flowable material or other type of material and be in liquid form, powder form, or other form. The impregnation process provides a cover member 14 that is generally saturated with the second material in one exemplary embodiment. The second material generally permeates the cover member 14 material. The porous nature of the cover member 14 in an exemplary embodiment provides for the necessary properties for sufficient impregnation of the second material in the cover member 14. It is understood that the entire cover member 14 may be impregnated with the second material 20 or only a portion of the cover member 14 can be impregnated. In another exemplary embodiment, a portion or portions of the cover member 14 are impregnated at strategic locations based on particular uses of the assembly, e.g., at a central location of the member 14, at distal ends of the member 14 or at other locations. The cover member 14 may also be impregnated with a plurality of materials selected to provide a desired reaction with the material contained in the glass ampoule 12.

As further shown in FIG. 2, the cover member 14 is initially a sleeve having open ends 22. As can be appreciated from FIGS. 2 and 3, the filled glass ampoule 12 is inserted into the open end 22 of the cover member 14. The open ends 22 are then sealed to form sealed ends 24 as shown in FIG. 3. The open ends 22 may be heat-sealed, adhesive-sealed or sealed using other processes. Accordingly, the dispenser assembly 10 is formed as shown in FIG. 3. It is also understood that a further outer packaging material 26 (shown schematically) may be provided over the dispenser assembly 10 for storage or shipping purposes and the like. It is further understood that the cover member 14 completely encapsulates the inner container 12 in an exemplary embodiment. In other embodiments, it is understood that the cover member 14 may partially cover the inner container 12.

It is understood that the flowable material 16 in the glass ampoule 12 and the material 20 impregnated into the cover member 14 are selected to provide a desired reaction. It is understood that the materials 16, 20 can be in liquid form, powder form, gaseous form, or solid form. In operation, after any outer packaging material 26 is removed, the glass ampoule 12 is ruptured by applying a force F through the cover member 14. For example, a user may apply finger-pressure by pinching or squeezing the glass ampoule 12 through the cover member 14. As further shown in FIG. 3, the glass ampoule 12 ruptures wherein the flowable material 16 exits the glass ampoule 12 and contacts the cover member 14. Upon contact with the cover member 14, the flowable material 16 associates with the second material 20 wherein a mixture M is formed. The mixture M generally resides with the cover member 14. It is understood that the cover member 14 is structured such that the mixture M can be sensed, accessed, detected, released or otherwise noticed through the cover member 14.

Such detection can take many forms. The mixture M may be dispensed from the cover member 14 such as if the cover member is generally saturated with the mixture M wherein the mixture M can drip from the cover member 14 or be wiped or otherwise transferred from the cover member 14. In one general sense, the mixture M may also be considered to be sensory detectable from the cover member 14. For example, the mixture M may be visually perceptible on the cover member 14. In one exemplary embodiment, the mixture M may change to a certain color or be in a glowing form. The mixture M may also be perceptible via an olfactory sense. The mixture M may also emit heat or be cool. In any of these configurations, it is considered a result of the activation of the dispenser assembly 10.

Thus, the dispenser assembly 10 provides a simple, easy to manufacture assembly 10. It is understood that the term "dispenser" can merely mean that the mixture M can be generally perceptible to the user (or sensed in any fashion), even if the mixture M is not transferred from the cover member 14. The assembly 10 can be easily operated and be provided for a wide variety of uses. In one exemplary embodiment, the dispenser assembly 10 may be used as an inhalant or for general aromatherapy. The assembly could also be used as a glow-member in the form of a light-stick or glow-stick. Other uses may also be possible such as described below.

Figure 4:
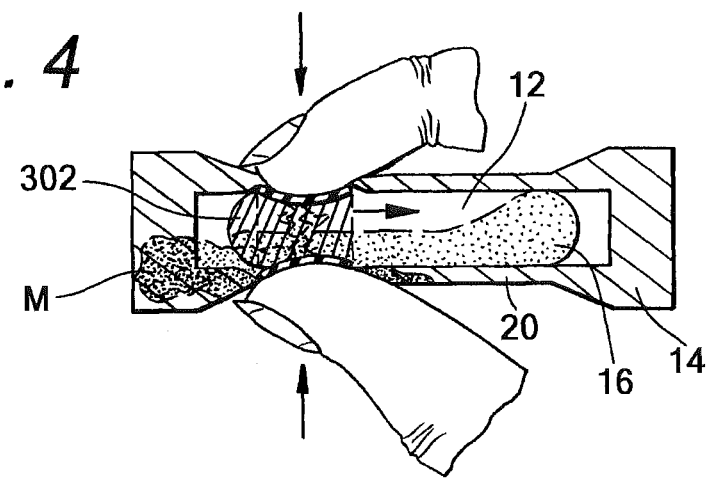
FIG. 4 is a schematic view of another embodiment of a dispenser assembly of the present invention wherein the inner container has a coating thereon.

FIG. 4 discloses another embodiment of the dispenser assembly 10. The inner container 12 in the form of the glass ampoule has a rubberized coating 302 thereon. It is understood from the arrow in FIG. 4 that the rubberized coating 302 may cover the inner container 12 more completely or cover the entire container 12. The coating 302 adheres to the glass shards from the container 12 when the container 12 is ruptured as shown in FIG. 4. This maintains the glass shards in a more confined area and prevents or minimizes the shards from possibly piercing through the cover member 14. The rubberized coating 302 can be made from various types of materials.

Figure 5:
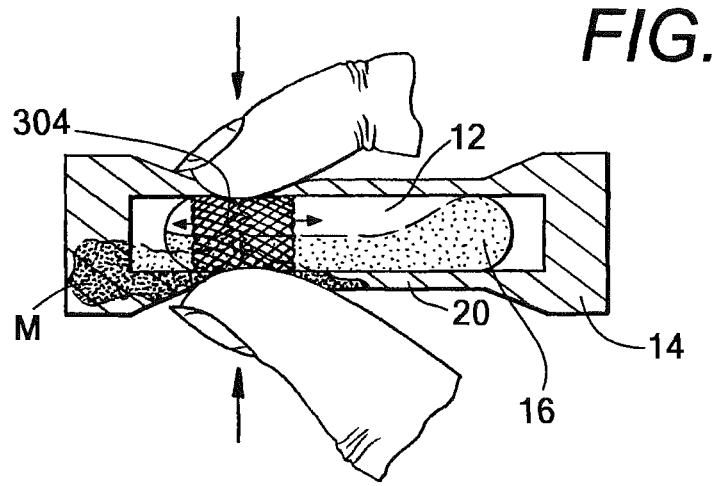
FIG. 5 is a schematic view of another embodiment of a dispenser assembly of the present invention wherein the inner container has a netting over the container.

FIG. 5 also discloses another alternative embodiment of the dispenser assembly 10. The inner container 12 in the form of the glass ampoule has a netting member 304. From the arrow in FIG. 5, it is understood that the netting will completely encapsulate the glass ampoule 12. The netting 304 has openings sized to allow the first material to pass therethrough upon rupture of the glass ampoule 12 but will generally contain the glass shards within the netting. This maintains the glass shards within the netting and prevents or minimizes the shards from possibly piercing through the cover member 14. It is understood that the netting may be made from non-absorbent material(s) so that the first material may freely pass by the netting 304 and react with the second material 20 associated with the cover member 14.

Figure 6:
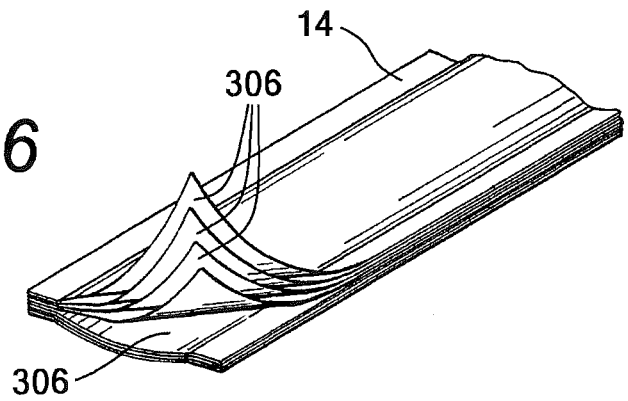
FIG. 6 shows an outer cover material having multiple layers that are impregnated with different materials.

FIG. 6 shows another embodiment of the cover member 14 that can be used in any embodiment of the dispenser assembly 10 of the present invention. The cover member 14 can be made of a plurality of layers 306. The number of layers can vary depending on a particular application. Each layer 306 may be impregnated with a different material. The materials used in the impregnation process are selected based on the desired result from a reaction with the first material contained in the inner container 12. Thus, in one exemplary embodiment, the cover member 12 may have two layers wherein one layer is impregnated with a second material and the other layer is impregnated with a third material. The second and third materials are selected to react with the first material in the inner container 12 to provide a desired reaction once the three materials mix together to form the mixture M.

Figure 7:
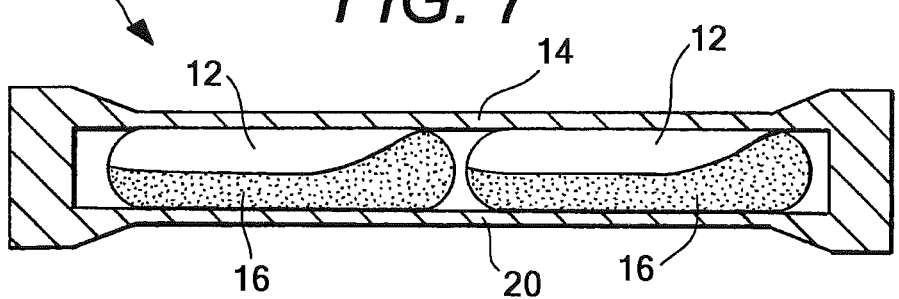
FIG. 7 is a schematic view of another embodiment of a dispenser assembly according to the present invention.
Figure 8:
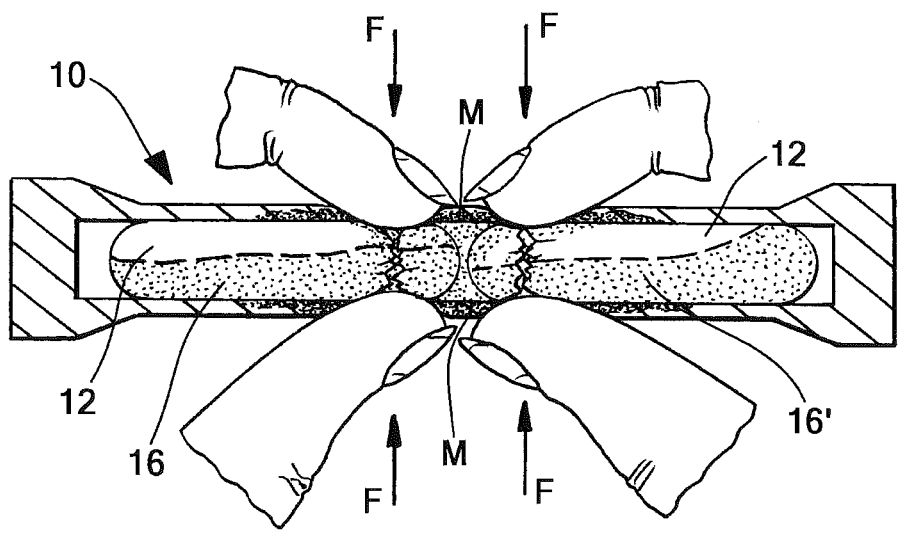
FIG. 8 is a schematic view of the dispenser assembly of FIG. 7 and showing rupture of multiple inner containers.

FIGS. 7 and 8 disclose another embodiment of the dispenser assembly of the present invention, also designated with the reference numeral 10. Similar elements are referred to with like reference numerals. In this embodiment, a plurality of inner containers 12 are contained within the cover member 14. Each inner container 12 contains a material wherein the second inner container contains a material 16' that is different from the material 16 in an exemplary embodiment. Also, in this embodiment, a pair of inner containers is provided. Additional containers holding materials can also be employed.

Connection and operation of the dispenser assembly 10 of FIGS. 7 and 8 is generally the same as described above. The user applies a force F to rupture each inner container. The materials 16, 16' mix together as well as with material 20 impregnated in the cover member 14. A mixture M is formed from the mixture of the materials 16, 16', 20. The materials are selected to provide a desired reaction.

FIGS. 9-11 disclose another embodiment of the dispenser assembly of the present invention and generally designated with the reference numeral 100. Similar elements will be referenced with similar reference numerals in the 100 series. The cover member 114 is generally the same as describe above. The inner container 112 is also a rupturable container. Rather than a glass ampoule, however, the inner container 112 is an injection molded container 112 having an outer wall 130 and a membrane 132 that cooperate to define a chamber 134. One end of the container 112 may be initially open to receive the first material 116 and then heat sealed to provide a closed chamber. The membrane 132 is a rupturable membrane that in an exemplary embodiment has a weld seam 136. As shown in FIGS. 9-11, the membrane 132 extends from the outer wall 130 at an angle and may be considered to be conical shaped. The inner container may be formed as described in U.S. patent application Ser. No. 12/362,062 which is expressly incorporated herein by reference and made a part hereof. The inner container may also take the form of the container disclosed in U.S. Pat. No. 6,641,319, which is expressly incorporated herein by reference and made a part hereof.

Connection and operation of the dispenser assembly 100 of FIGS. 9-11 is generally the same as described above. The inner container 112 is contained within the cover member 114 that is impregnated with the second material 120. The user applies a force F to the membrane 132 through the cover member 114. The force F ruptures the membrane along the weld seam 136 to rupture the inner container. The material 116 exits the inner container 112 and contacts the cover member 114 and mixes with the second material 120. A mixture M is formed from the mixture of the materials 116, 120. The materials are selected to provide a desired reaction.

FIGS. 12 and 13 disclose another embodiment of the dispenser assembly of the present invention and generally designated with the reference numeral 200. Similar elements will be referenced with similar reference numerals in the 200 series. The cover member 214 is generally the same as describe above. The inner container 212 is also a rupturable container. Similar to FIGS. 9-11, the inner container 212 is an injection molded container 212 having an outer wall 230 and a pair of membranes 232, 233 as well as a dividing wall 238 that cooperate to define a first chamber 234 and a second chamber 235. One end of the container 212 may be initially open to receive the materials 216, 216' contained in the first chamber 234 and the second chamber 235 respectively. The open ends are then sealed to provide closed chambers 234, 235. The membranes 232, 233 are rupturable membranes that in an exemplary embodiment have weld seams 236. As shown in FIGS. 12-13, the membranes 232, 233 extend from the outer wall 230 at an angle and may be considered to be conical shaped. The inner container 212 may be formed as described in U.S. patent application Ser. Nos. 12/362,062 and 11/414,154 which applications are expressly incorporated herein by reference and made a part hereof.

Connection and operation of the dispenser assembly 200 of FIGS. 12-13 is generally the same as described above. The inner container 212 is contained within the cover member 214 that is impregnated with the second material 220. The user applies a force F to the membranes 232, 233 through the cover member 214. The force F ruptures the membranes 232, 233 along the weld seams 236 to rupture the inner container 212. The materials 216, 216' exit the inner container 212 and mix with one another as well as contact the cover member 214. The materials 216, 216' mix with the second material 220. A mixture M is formed from the mixture of the materials 216, 216', 220. The materials are selected to provide a desired reaction.

It is understood that in an exemplary embodiment, the containers may have a cylindrical shape. Other shapes and configurations are also possible.

It is understood that the "first" and "second" designations for the dispenser of the present invention can be reversed as desired. It is further understood that the term "outer" when describing the outer wall of the dispenser is a relative term. It is understood that the dispenser of the present invention could be incorporated into other structures that may encompass the outer wall. The outer wall of the dispenser of the present invention, cooperates with the membrane and dividing wall in certain embodiments to define the chambers of the dispenser.

The dispenser assembly of the present invention is designed to primarily contain materials separately and then mix the materials upon activation to provide a desired reaction that can be perceived by the user. The materials used can vary depending on the desired reaction or ultimate use. In one particular application, the assembly can be used as an inhalant. The glass ampoule contains a first material while the cover member is impregnated with a second material. As described above, the glass ampoule is ruptured so that the first material from the ampoule can react with the second material impregnated in the cover member. In another application, the assembly can be used in aromatherapy applications where the first material and second material are maintained separate from one another until a user desires activation. Similar to aromatherapy applications, the assembly can also be used in two-part fragrance applications where it is desirable to maintain materials separated until a user is ready for activation. For example, an oil material can be maintained separate from a fragrance material until such time a user is ready for the two materials to come in contact with one another and react to provide the desired result. Activation is consistent with the discussion above. Such configuration extends the life of the desired fragrance or aromatherapy etc. Also, the assembly can be used in glue and adhesive diagnostics wherein materials are kept separate until activation. The assembly can also be used as a light-stick or glow-stick embodiment. In addition, it is understood that the term dispenser assembly has broad meaning wherein upon reaction of the materials, a desired state is sensed. This is the case even if the resulting mixture created by the interaction of the first material with the second material is not actually transferred from the assembly. In some embodiments, all that is desired is for the user to sense, in some fashion, the interaction of the materials.

Also, the dispenser assembly of the present invention utilizing multiple materials to react with one another can be used for a wide variety of uses. The following is a non-exhaustive discussion regarding the many possible uses for the dispenser assembly of the present invention. It is understood that related uses to those described below are also possible with the dispenser.

In one example, the dispenser of the present invention can be used in a two-part hair care product such as a hair dye kit. A first flowable substance of the hair dye kit can be carried in the first chamber, and a second flowable substance of the hair dye kit can be carried in the second chamber. The membrane is ruptured wherein the two flowable substances can be mixed together to form a mixture or solution. The mixture or solution can then be dispensed from the dispenser onto the hair of a user. In a multitude of other examples, the dispenser can dispense a flowable material or mixture that is an adhesive, epoxy, or sealant, such as an epoxy adhesive, craft glue, non-medical super glue and medical super glue, leak sealant, shoe glue, ceramic epoxy, fish tank sealant, formica repair glue, tire repair patch adhesive, nut/bolt locker, screw tightener/gap filler, super glue remover or goo-b-gone. Also, the dispenser can dispense a flowable material or mixture that is an automotive product, such as a rear view mirror repair kit, a vinyl repair kit, an auto paint touch up kit, a window replacement kit, a scent or air freshener, a windshield wiper blade cleaner, a lock de-icer, a lock lubricant, a liquid car wax, a rubbing compound, a paint scratch remover, a glass/mirror scratch remover, radiator stop-leak, or a penetrating oil. The dispenser can also dispense a flowable material or mixture that is a chemistry material, such as a laboratory chemical, a fish tank treatment, a plant food, a cat litter deodorant, a buffer solution, a rehydration solution of bacteria, a biological stain, a rooting hormone, a colorant dispenser, or disinfectants.

Moreover, the dispenser can dispense a flowable material or mixture that is a cosmetic, fragrance or toiletry, such as nail polish, lip gloss, body cream, body gel, hand sanitizer, cologne, perfume, nail polish remover, liquid soaps, skin moisturizers, tooth whiteners, hotel samples, mineral oils, toothpastes, or mouthwash. The dispenser can also dispense a flowable material or mixture that is an electronics product, such as a cleaning compound, a telephone receiver sanitizer, a keyboard cleaner, a cassette recorder cleaner, audio/video disc cleaner, a mouse cleaner, or a liquid electrical tape. In addition, the dispenser can dispense a flowable material or mixture that is a food product, such as food colorings, coffee flavorings, spices, food additives, drink additives, confections, cake gel, sprinkles, breath drops, condiments, sauces, liquors, alcohol mixes, energy drinks, or herbal teas and drinks. The dispenser assembly can also dispense a flowable material or mixture that is a hair care product, such as hair bleaches, hair streaking agent, hair highlighter, shampoos, hair colorants, conditioners, hair gels, mousse, hair removers, or eyebrow dye. The dispenser can also dispense a flowable material that is a home repair product, such as a caulking compounds or materials, a scratch touch up kit, a stain remover, a furniture repair product, a wood glue, a patch lock, screw anchor, wood tone putty or porcelain touch-up.

In addition, the dispenser assembly can dispense a flowable material or mixture that is a test kit, such as a lead test kit, a drug kit, a radon test kit, a narcotic test kit, a swimming pool test kit (e.g., chlorine, pH, alkalinity etc.), a home water quality tester, a soil test kit, a gas leak detection fluid, or a pregnancy tester. The dispenser can dispense a large variety of lubricants including industrial lubricants, oils, greases, graphite lubricants or a dielectric grease. The dispenser can also dispense a flowable material or mixture that as part of a medical device test kit, such as a culture media, a drug monitoring system, a microbiological reagent, a streptococcus test kit, or a residual disinfectant tester. In addition, the dispenser 10 can dispense a large variety of medicinal products, such as blister medicines, cold sore treatments, insect sting and bit relief products, skin cleaning compounds, tissue markers, topical antimicrobials, topical demulcent, treatments for acne such as acne medications, umbilical area antiseptics, cough medicines, waterless hand sanitizers, toothache remedies, cold medicines and sublingual dosages. Furthermore, the dispenser can dispense a flowable material or mixture that is a novelty product, such as a chemiluminescent light, a Christmas tree scent, a glitter gel, and a face paint. The dispenser can also dispense a variety of paint products such as novelty paints, general paints, paint additives, wood stain samples, caulk, paint mask fluid or paint remover. The dispenser can also dispense a flowable material or mixture that is a personal care product, such as shaving cream or gel, aftershave lotion, skin conditioner, skin cream, skin moisturizer, petroleum jelly, insect repellant, personal lubricant, ear drops, eye drops, nose drops, corn medications, nail fungal medication, aging liquids, acne cream, contact lens cleaner, denture repair kit, finger nail repair kit, liquid soaps, sun screen, lip balm, tanning cream, self-tanning solutions or homeopathic preparations. A large variety of pest control products can be dispensed by the dispenser, including insect attractants, pesticides, pet medications, pet insect repellants, pet shampoos, pest sterilizers, insect repellants, lady bug attractant and fly trap attractant. Various safety products can be dispensed through the dispenser including respirator tests and eye wash solution.

The dispenser assembly can also dispense a large variety of stationery or craft products, such as magic markers, glitter gels, glitter markers, glitter glues, gel markers, craft clues, fabric dyes, fabric paints, permanent markers, dry erase markers, dry eraser cleaner, glue sticks, rubber cement, typographic correction fluids, ink dispensers and refills, paint pens, counterfeit bill detection pen, envelope squeeze moisturizers, adhesive label removers, highlighters, and ink jet printer refills. The dispenser can also dispense various vitamins, minerals, supplements and pet vitamins. The dispenser can also dispense a flowable material or mixture in a variety of other applications such as for aroma therapy products, breathalyzer tests, wildlife lures, eyeglass cleaners, portable lighting fuels, bingo and other game markers, float and sinker devices, toilet dyes and treatments, dye markers, microbiological reagents, shoe polishes, clothing stain removers, carpet cleaners and spot removers, tent repair kits, plumbing flux applicator, rust remover, tree wound treatment, animal medicine dispenser, animal measured food dispenser, odor eliminator liquids, multi-purpose oils, ultrasonic cleaner concentrate, manufacturing parts assembly liquids and irrigation solutions. In addition, the dispenser can be used as, or in connection with a suction device for culture sampling, taking various liquid samples, taking various swabbing samples and for acting as a chemical tester, such as may be used for testing drinks for various "date rape" drugs. In addition, the dispenser can dispense a variety of sports products including sports eye black, football hand glue, and baseball glove conditioner and pine tar. The dispenser can dispense any variety of flowable materials including liquids and powders, and further including a liquid and a powder, two or more powders, or two or more liquids. The dispenser may be used as part of 2-part system (mix before use) including a liquid with a powder, a liquid with a liquid, a powder with a powder, or sealed inside another tube or product container or partially sealed, connected or attached to another container. The dispenser may also be used as part of a plunger dispensing system and diagnostic testing.

The dispenser assembly of the present invention may also be used for windshield wiper blade cleaner and other automotive applications, fragrances, pastry gels, eyebrow dye, paints, hair paints, finger nail repair kit, animal medicine dispenser, animal food dispenser, culture media samples, drug test kits, and chemical testers (e.g. date rape etc.). As an illustration, although the applicator has been described as being utilized for mechanical uses, it can similarly be used for applying adhesives, mastic or the like. The dispenser may also be used in diagnostic testing kits, explosive testing kits or other test kits.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. A dispenser assembly comprising:
   a glass ampoule containing a first flowable material; and
   a paper-based porous cover member encapsulating the glass ampoule, the cover member being impregnated with a second material, wherein the glass ampoule is rupturable wherein the first flowable material contacts the cover member and interacts with the second material to form a mixture, wherein the glass ampoule has a netting over the glass ampoule, and wherein the netting is non-absorbent and has an opening sized to allow the first flowable material to pass therethrough and to hold glass shards produced from the ruptured glass ampoule within the netting.

2. The dispenser assembly of claim 1 wherein the mixture is capable of being dispensed from the cover member.

3. The dispenser assembly of claim 1 wherein the mixture is sensory detectable from the cover member.

4. The dispenser assembly of claim 1 wherein the mixture is visually perceptible on the cover member.

5. The dispenser assembly of claim 1 wherein mixture is perceptible via an olfactory sense.

6. The dispenser assembly of claim 1 wherein the mixture emits heat.

7. The dispenser assembly of claim 1 wherein the mixture is cool.

8. The dispenser assembly of claim 1 wherein the first flowable material is a liquid and the second material is a powder contained within the cover member.

9. The dispenser assembly of claim 1 wherein the entire cover member is impregnated with the second material.

10. The dispenser assembly of claim 1 wherein the cover member comprises a plurality of layers, each layer being impregnated with a different material.

11. The dispenser assembly of claim 1 wherein the cover member has a first layer and a second layer, the first layer being impregnated with the second material and the second layer being impregnated with a third material, the third material being different from the second material.

12. The dispenser assembly of claim 1 wherein the glass ampoule comprises a plurality of glass ampoules, each containing a flowable material.

13. The dispenser assembly of claim 1 wherein the glass ampoule has a rubberized coating thereon.

14. The dispenser assembly of claim 1 wherein the cover member is cellulose acetate.

15. A dispenser assembly comprising:
   a glass ampoule containing a first flowable material, the glass ampoule having a non-absorbent netting over the glass ampoule; and
   a paper-based porous cover member encapsulating the netting and glass ampoule, the cover member being impregnated with a second material, wherein the glass ampoule is rupturable and wherein the netting has openings sized to allow the first flowable material to pass therethrough and to hold glass shards produced from the ruptured glass ampoule within the netting, and wherein the first flowable material contacts the cover member and interacts with the second material to form a mixture.

* * * * *